US009282884B2

(12) United States Patent
Kato et al.

(10) Patent No.: US 9,282,884 B2
(45) Date of Patent: Mar. 15, 2016

(54) OPHTHALMIC APPARATUS

(71) Applicant: Tomey Corporation, Nagoya (JP)

(72) Inventors: Chihiro Kato, Nagoya (JP); Yuji Nozawa, Nagoya (JP)

(73) Assignee: TOMEY CORPORATION, Nagoya (JP)

( * ) Notice: Subject to any disclaimer, the term of this patent is extended or adjusted under 35 U.S.C. 154(b) by 15 days.

(21) Appl. No.: 13/782,074

(22) Filed: Mar. 1, 2013

(65) Prior Publication Data

US 2013/0229627 A1 Sep. 5, 2013

(30) Foreign Application Priority Data

Mar. 2, 2012 (JP) ................................. 2012-046858

(51) Int. Cl.
*A61B 3/10* (2006.01)
*A61B 3/00* (2006.01)
*A61B 3/12* (2006.01)

(52) U.S. Cl.
CPC ............... *A61B 3/0008* (2013.01); *A61B 3/102* (2013.01); *A61B 3/1005* (2013.01); *A61B 3/12* (2013.01)

(58) Field of Classification Search
CPC .... A61B 3/0008; A61B 3/102; A61B 5/0066; G01B 9/02091; G01B 9/02004; G01B 9/02027; G01B 9/02028; G01B 9/02044; G01B 9/02063; G01B 9/02068; G01B 9/02072; G01B 9/02074; G01B 9/02083

USPC .......... 356/451, 479, 491, 512, 497; 600/156; 378/4; 398/17; 351/205, 246, 206, 208, 351/220; 250/252.1

See application file for complete search history.

(56) References Cited

U.S. PATENT DOCUMENTS

| | | | |
|---|---|---|---|
| 2007/0127033 A1* | 6/2007 | Ueno | 356/497 |
| 2008/0159468 A1* | 7/2008 | Chong | 378/4 |
| 2008/0180683 A1* | 7/2008 | Kemp | 356/491 |
| 2009/0046295 A1* | 2/2009 | Kemp et al. | 356/479 |
| 2009/0261240 A1* | 10/2009 | Watanabe et al. | 250/252.1 |
| 2010/0272432 A1* | 10/2010 | Johnson | 398/17 |
| 2011/0134436 A1* | 6/2011 | Podoleanu et al. | 356/512 |
| 2011/0157597 A1* | 6/2011 | Lu et al. | 356/479 |
| 2011/0190586 A1* | 8/2011 | Kemp | 600/156 |
| 2011/0255095 A1* | 10/2011 | Jiang et al. | 356/479 |
| 2011/0292395 A1* | 12/2011 | Fercher et al. | 356/451 |
| 2013/0185023 A1* | 7/2013 | Vakoc et al. | 702/189 |

* cited by examiner

*Primary Examiner* — Bumsuk Won
*Assistant Examiner* — Collin X Beatty
(74) *Attorney, Agent, or Firm* — Vierra Magen Marcus LLP

(57) ABSTRACT

An ophthalmic apparatus is provided with a light source, an optical measurement system, an optical reference system, an optical calibration system, a light receiving element, and a processor. The light receiving element receives an interference light for measurement produced by both the reflected light guided by the optical measurement system and the reference light guided by the optical reference system, and also receives an interference light for calibration produced by the calibration light guided by the optical calibration system and the reference light guided by the optical reference system. The processor determines a position of a measuring portion inside an eye to be examined by Fourier-analyzing the interference light for measurement and the interference light for calibration.

5 Claims, 5 Drawing Sheets

OPHTHALMIC APPARATUS

CROSS-REFERENCE TO RELATED APPLICATION

This application claims priority to Japanese Patent Application No. 2012-46858, filed on Mar. 2, 2012, the contents of which are hereby incorporated by reference into the present application.

1. Technical Field

The present teachings relate to an ophthalmic apparatus for examining an eye to be examined.

2. Description of Related Art

Japanese Patent Application Publication No. 2007-37984 discloses an ophthalmic apparatus for examining an interior (e.g., crystalline lens, retina) of an eye to be examined. This ophthalmic apparatus is equipped with an optical measurement system for radiating light from a light source to the interior of the eye and guiding the reflected light, and an optical reference system for radiating light from the light source to a reference surface and guiding the reflected light, A position of a measuring portion (e.g., the crystalline lens, the retina) inside the eye is determined from interference light produced by both the reflected light guided by the optical measurement system and the reflected light guided by the optical reference system.

BRIEF SUMMARY

Methods of examining an interior of an eye to be examined by using interference light includes a time domain method and a Fourier domain method. As compared with the time domain method, since the Fourier domain method uses Fourier analysis, it has an advantage in that a configuration of an optical system can be simplified. However, in an ophthalmic apparatus of the Fourier domain method, it has been proved that a position of a measuring portion inside the eye determined from interference light is changed as time passes. That is, when properties of light radiated from a light source to the eye are changed due to temperature change or aging change of the light source, properties of interference light received by a light receiving element are also changed. As a result, a position of a measuring portion inside the eye obtained by Fourier-analyzing the received interference light is also changed.

It is an object of the present teachings to provide an ophthalmic apparatus capable of accurately determining a position of a measuring portion inside an eye to be examined even when properties of interference light are changed as time passes.

The ophthalmic apparatus disclosed in the present specification includes a light source, an optical measurement system, an optical reference system, an optical calibration system, a light receiving element, and a processor. The optical measurement system is configured to radiate light from the light source to an interior of an eye to be examined and guide reflected light from the eye. The optical reference system is configured to guide the light from the light source as reference light. The optical calibration system is configured to guide the light from the light source as calibration light. The light receiving element is configured to receive interference light for measurement produced by both the reflected light guided by the optical measurement system and the reference light guided by the optical reference system, and also receive interference light for calibration produced by both the calibration light guided by the optical calibration system and the reference light guided by the optical reference system. The processor determines a position of a measuring portion inside the eye by Fourier-analyzing the interference light for measurement and the interference light for calibration received by the light receiving element.

The ophthalmic apparatus includes the optical calibration system in addition to the optical measurement system and the optical reference system. Accordingly, the position of the measuring portion determined from the interference light for measurement can be corrected by using the interference light for calibration. As a result, even when the position of the measuring portion determined from the interference light for measurement is changed as time passes, the position of the measuring portion can be accurately specified.

DETAILED DESCRIPTION OF EMBODIMENTS

Figure 1:
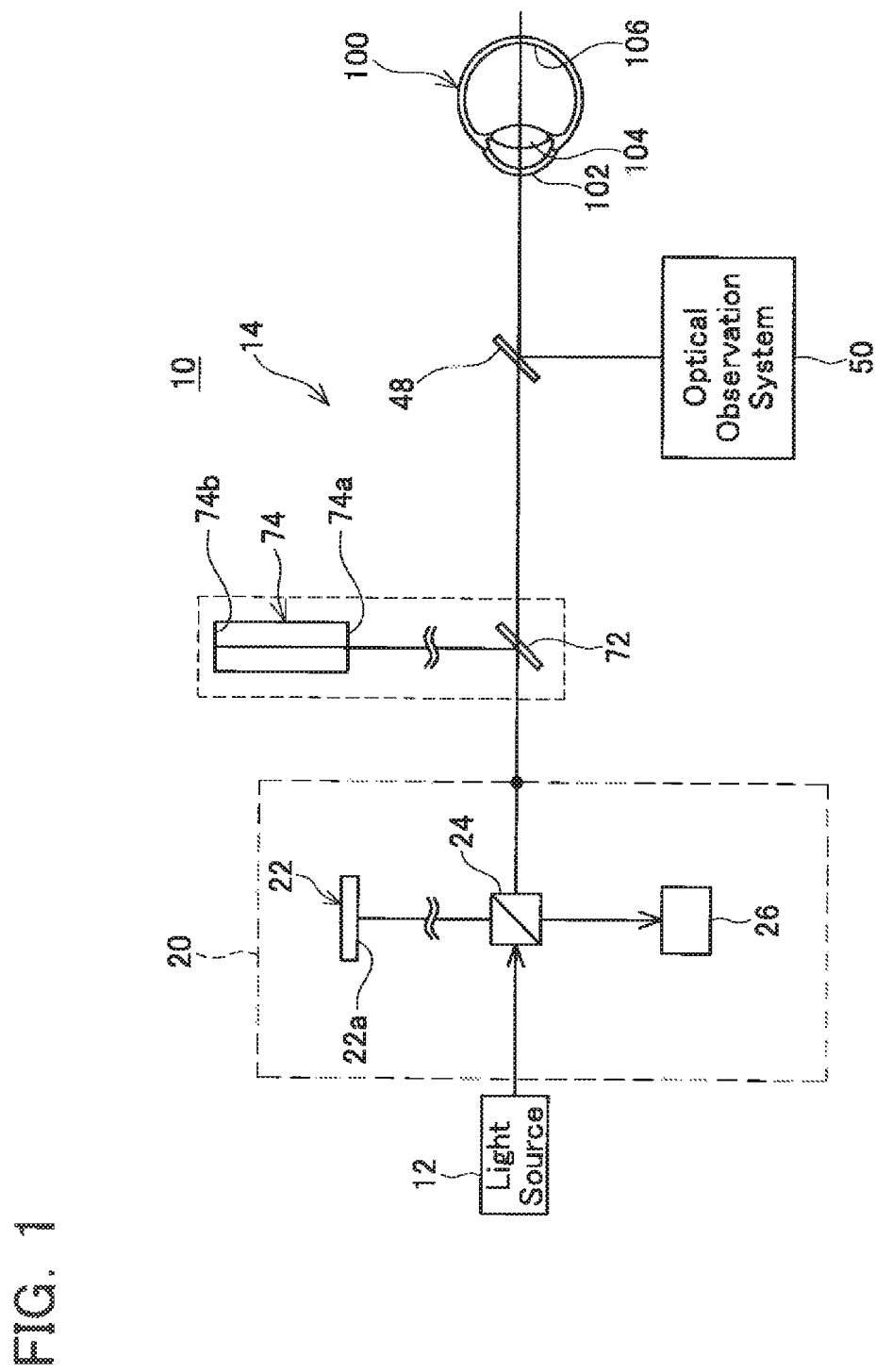
FIG. 1 is a diagram schematically showing a configuration of an optical system If an ophthalmic apparatus according to an embodiment.

In one aspect of the present teachings, the optical calibration system may be designed such that an optical path length from 0 point where an optical path length of the optical reference system and an optical path length of an optical object system match is set to be a predetermined length. According to such a configuration, a signal having a peak at a predetermined position with respect to the 0 point can be obtained.

In another aspect of the present teachings, the processor may correct the position of the measuring portion inside the eye to be examined determined from the interference light for measurement by using a result measured from the interference light for calibration. According to such a configuration, the position of the measuring portion determined from the interference light for measurement can be adequately corrected. For example, when properties of light radiated from the light source is changed as time passes, the interference light for calibration received by the light receiving element is also changed. On the other hand, the optical path length of the optical calibration system is set to be a predetermined value. Therefore, the position of the measuring portion inside the eye to be examined determined from the interference light for measurement can be adequately corrected based on a result measured from the interference light for calibration.

In another aspect of the present teachings, the optical calibration system may include a first optical path section set to have a first optical path length from the 0 point, and a second optical section set to have a second optical path length from the 0 point. The light receiving element may receive first interference light for calibration produced by light guided by the first optical path section of the optical calibration system and reflected light guided by the optical reference system, and second interference light for calibration produced by light guided by the second optical path section of the optical calibration system and reflected light guided by the optical reference system. The processor may correct the position of the measuring portion inside the eye to be examined determined from the interference light for measurement by using a result measured from the first interference light for calibration and a result measured from the second interference light for calibration. According to such a configuration, the position of the measuring portion of the eye can be corrected by using d difference between the optical path length of the first optical path section and the optical path length of the second optical path section. As a result, for example, even when the optical path length of the optical system is changed over a period of time due to aging, when the change in the optical path length of the first optical path section and the change in the optical path length of the second optical path section are identical to each other, the changes can be canceled out by subtracting one of the changed optical length from the other changed optical length. Therefore, the position of the measuring portion inside the eye can he adequately determined by using the optical path difference between the first optical path section and the second optical path section.

In another aspect of the present teachings, the processor may further calculate an ocular axial length of the eye using a position of a cornea and a position of a retina of the eye determined from the interference light for measurement and the interference light for calibration. According to such a configuration, the ocular axial length of the eye to be examined can be accurately calculated.

(Embodiment)

As shown in FIG. 1, an ophthalmic apparatus according to a representative embodiment of the present teachings includes a measuring unit 10 for examining an eye 100 to be examined. The measuring unit 10 includes an optical interference system 14 for causing interference between reflected light reflected from the eye 100 and reference light, an optical observation system 50 for observing an anterior eye part of the eye 100 to be examined, and an optical alignment system (not shown) for aligning the measuring unit 10 with respect to the eye 100 to be examined such that the measuring unit 10 exhibits a predetermined positional relationship with the eye 100 to be examined. An optical alignment system used in a known ophthalmic apparatus may be utilized as the optical alignment system, hence the detailed description thereof will be omitted.

The optical interference system 14 includes an light source 12, an optical measurement system (24, 72, 48) for radiating light from the light source 12 to the interior of the eye 100 to be examined and guiding reflected light from the eye 100, an optical reference system (24, 22) for radiating light from the light source 12 on a reference surface 22a and guiding reflected light therefrom, an optical calibration system (24, 72, 74) for radiating light from the light source 12 on reflection surfaces (74a, 74b) and guiding reflected light therefrom, and a light receiving element 26 for receiving interference light for measurement between the reflected light guided by the optical measurement system and the reflected light guided by the optical reference system, and interference light for calibration produced both by the reflected light guided by the optical calibration system and the reflected light guided by the optical reference system.

The light source 12 is a light source of a wavelength sweep type, and a wavelength of light to be radiated is to be changed at a predetermined cycle. That is, in the ophthalmic apparatus according to the embodiment, the light radiated from the light source 12 is radiated to the eye 100 to be examined while changing its wavelength (scanning). Then, intensity distribution of the light reflected from each portion of the eye 100 in a depth direction is obtained by Fourier-analyzing a signal Obtained from interference light produced by the reflected light from the eye 100 and reference light When the light intensity distribution of the eye 100 in the depth direction is obtained, it becomes possible to specify a position of each portion (that is, a crystalline lens 104 and a retina 106) inside the eye 100 as described below. Note that, the light radiated from the light source 12 is changed depending on temperature of the light source 12 and aging change of the light source 12. Accordingly, when the temperature of the light source 12 is increased depending on measuring time, properties of light radiated from the light source 12. are changed. Properties of light radiated from the light source 12 are changed also by aging change of the ophthalmic apparatus. As a result, a result of Fourier analysis of a signal obtained from interference light is also changed.

The optical measurement system includes a beam splitter 24, a beam splitter 72, and a hot mirror 48. The light radiated from the light source 12 is radiated to the eye 100 via the beam splitter 24, the beam splitter 72, and the hot mirror 48. The reflected light from the eye 100 is guided to the light receiving clement 26 via the hot mirror 48, the beam splitter 72 and the beam splitter 24.

The optical reference system includes the beam splitter 24 and the reference mirror 22. Some of the light radiated from the light source 12 is reflected by the beam splitter 24, radiated on a reference surface 22a of the reference mirror 22, and reflected by the reference surface 22a of the reference mirror 22. The light reflected by the reference mirror 22 is guided to the light receiving element 26 via the beam splitter 24. The reference mirror 22, the beam splitter 24, and the light receiving element 26 are disposed in an interferometer 20, and their positions are fixed. Accordingly, in the ophthalmic apparatus according to the embodiment, a reference optical path length of the optical reference system is constant and is not changed.

The calibration system includes the beam splitter 24, the beam splitter 72, and an optical member 74. The light radiated from the light source 12 is radiated to the optical member 74 via the beam splitter 24 and the beam splitter 72. The optical member 74 has a first reflection surface 74a provided on an end thereof and a second reflection surface 74b provided on the other end thereof Accordingly, some of the light radiated to the optical member 74 is reflected by the first reflection surface 74a and remaining light is introduced in the optical member 74. Some of the light introduced in the optical member 74 is reflected by the second reflection surface 74b and remaining light is radiated outside form the optical member 74. The light reflected by the first reflection surface 74a and the light reflected by the second reflection surface 74b is guided to the light receiving element 26 via the beam splitter 72 and the beam splitter 24.

Figure 3:
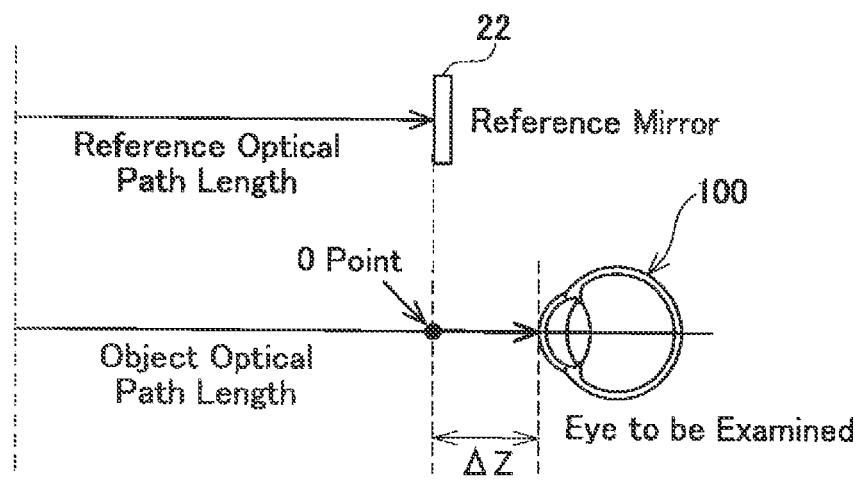
FIG. 3 is a diagram for illustrating a positional relationship of 0 point, a reference mi and an eye to be examined.

The optical calibration system according to the embodiment has a first optical path section (i.e., light source 12→first reflection surface 74a→light receiving element 26) set to have a first optical path length from 0 point, and a second optical path section (i.e., light source 12→second reflection surface 74b→light receiving element 26) set to have a second optical path length from the 0 point. Specifically, a position of the optical member 74 is set based on the 0 point, and an optical path length from the 0 point to the first reflection surface 74a and an optical path length from the 0 point to the second reflection surface 74b are set longer than a distance from the 0 point to the retina of the eye 100. Herein, the 0 point denotes a point where an optical path length of the optical reference system (reference optical path length) and an optical path length of an optical object system (object optical path length) match (see FIG. 3). As is apparent from the above description, a difference of the optical path lengths of the fist optical path section and the second optical path section is determined by a length from the first reflection surface 74a, which is an end of the optical member 74, to the second reflection surface 74b, which is the other end of the optical member 74. That is, the difference of the optical path lengths of the first optical path section and the second optical path section is not influenced by a positional relationship between the optical member 74 and other members, and is determined only by the optical member 74. Accordingly, the difference of the optical path lengths of the first optical path section and the second optical path section can be managed with a high accuracy by increasing shape accuracy of the optical member 74.

Note that, for example, an optical glass may be used for the optical member 74. By radiating light from the light source 12 to the optical glass, an end of the optical glass (incident surface) can be functioned as the first reflection surface and the other end of the optical glass (emission surface) can be functioned as the second reflection surface. Another example of the optical member 74 includes, for example, an optical plastic.

The light receiving element 26 detects interference light for measurement between the light guided by the optical reference system and the light guided by the optical measurement system, and interference light for calibration produced by both the light guided by the optical reference system and the light guided by the optical calibration system. As is apparent from the above description, the interference light for calibration includes first interference light for calibration produced by both the light reflected by the first reflection surface 74a (i.e., light guided by the first optical path section), and light guided by the optical reference system, and second interference light for calibration produced by both the light reflected by the second reflection surface 74b (i.e., light guided by the second optical path section) and the light guided by the optical reference system. Accordingly, the light receiving element 26 detects the interference light for measurement, the first interference light for calibration, and the second interference light for calibration. For example, a photodiode may be used for the light receiving element 26.

The optical observation system 50 radiates observation light to the eye 100 via the hot mirror 48 and images reflected light reflected from the eye 100 (that is reflected light of the radiated observation light). Herein, the hot mirror 48 transmits the light from the light source 12 of the optical interference system while reflecting the light from the light source of the optical observation system 50. Accordingly, in the ophthalmic apparatus according to the embodiment, measurement by the optical interference system and the observation of an anterior eye part by the optical observation system 50 can be executed at a same time. Note that since an optical observation system used in a known ophthalmic apparatus may be utilized as the optical observation system 50, detailed description of a configuration thereof will be omitted.

Figure 2:
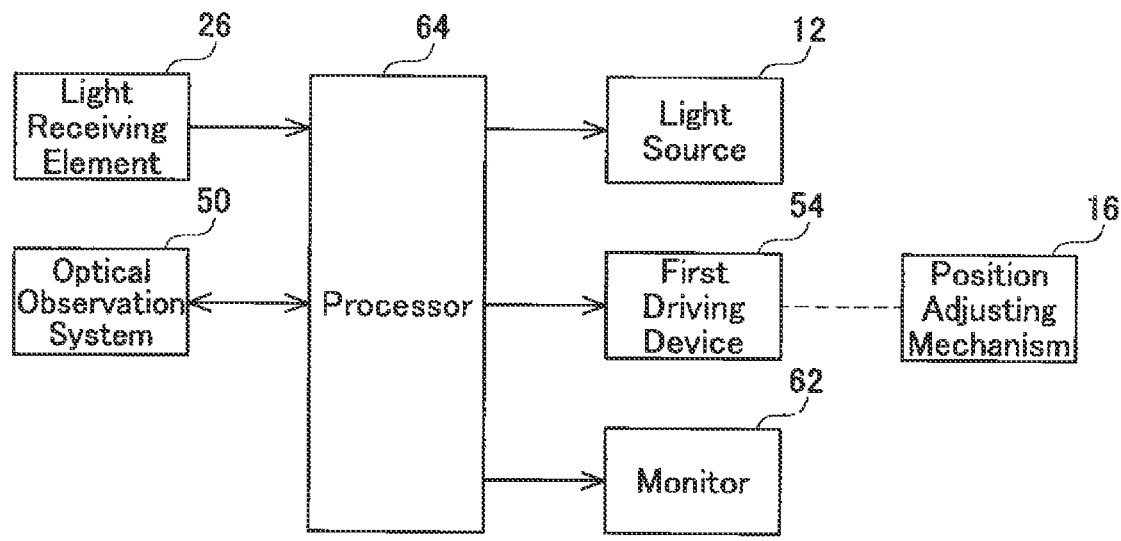
FIG. 2 is a block diagram of a control system of the ophthalmic apparatus according to the embodiment.

Note that the ophthalmic apparatus according to the embodiment includes a position adjusting mechanism 16 for adjusting a position of the measuring unit 10 with respect to the eye 100 (see FIG. 2) and a first driving device 54 for driving the position adjusting mechanism 16 (see FIG. 2). The position of the measuring unit 10 with respect to the eye 100 is adjusted by driving the first driving device 54.

Next, a configuration of a control system of the ophthalmic apparatus according to the embodiment will be described. As shown in FIG. 2, the ophthalmic apparatus is controlled by a processor 64. The processor 64 includes a microcomputer (microprocessor) comprising a CPU, a ROM, a RAM, etc., and a gate array for high-speed computing. The light source 12, the first driving device 54, a monitor 62, and the optical observation system 50 are connected to the processor 64. The processor 64 controls on/off of the light source 12, drives the position adjusting mechanism 16 by controlling the first driving device 54, and controls the optical observation system 50 to display the anterior eye part imaged by the optical observation system 50 on the monitor 62. The light receiving element 26 is also connected to the processor 64, and an interference signal depending on the intensity of the interference light (i.e., interference light for measurement, first interference light for calibration, second interference light for calibration) detected by the light receiving element 26 is input to the processor 64. The processor 64 specifies positions of portions of the eye 100 (e.g., front and rear surfaces of the cornea 102, front and rear surfaces of the crystalline lens 104, a surface of the retina 106) and the reflection surfaces 74a and 74b of the optical member 74 by Fourier transforming the interference signal from the light receiving element 26, and calculates an ocular axial length of the eye 100 using the specified positions. Note that a detail of processing for specifying the positions of respective measurement portions of the eye 100 by the processor 64 will be described below.

Figure 5:
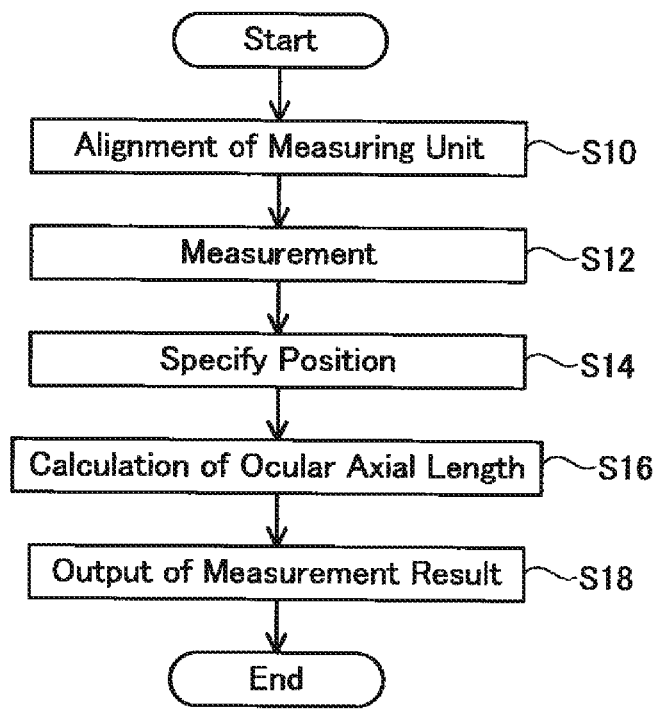
FIG. 5 is a flow chart showing an example of a processing procedure of the ophthalmic apparatus according to the embodiment.

Next, a procedure of measuring the ocular axial length by using the ophthalmic apparatus according to the embodiment will be described. As illustrated in FIG. 5, first, a user operates an operation member such as a joystick (not shown) to perform alignment of the measuring unit 10 with respect to the eye 100 (S10). That is, the processor 64 drives the position adjusting mechanism 16 by the first driving device 54 depending on the operation of the operation member by the user. Herewith, a position of the measuring unit 10 with respect to the eye 100 in xy directions (vertical and horizontal directions) and a z direction (direction of back and forth motion) is adjusted. Furthermore, the processor 64 adjusts a focal point adjusting mechanism and a 0 point adjusting mechanism (not shown) so that a position of a focal point of light radiated to the eye 100 from the light source 12 becomes a predetermined position of the eye 100 (e.g., front surface of the cornea 102), and the position of the 0 point where the object optical path length and the reference optical path length match becomes a predetermined position with respective to the eye 100 (e.g., a position slightly deviated on the light source 12 side from the front surface of the cornea 102). Note that the position of the 0 point may be adjusted so that the 0 point may be at a position slightly deviated from the retina 106 in a direction apart from the light source 12.

Next, the processor 64 acquires a signal detected by the light receiving element 26 while changing frequency of the light radiated from the light source 12 (S12). As is already described, light reflected from each portion of the eye 100 in the depth direction is included in the interference light received by the light receiving element 26. That is, the interference signal output from the light receiving element 26 becomes a signal of which signal intensity is changed depending on time as shown in FIG. 4, and the signal includes a signal depending on an interference wave produced by both the reference light and reflected light reflected from the respective portions of the eye 100 (i.e., the front surface and rear surface of the cornea 102, the front surface and rear surface of the crystalline lens 104, the surface of the retina 106) and first and second reflection surfaces 74a and 74b.

Figure 4:
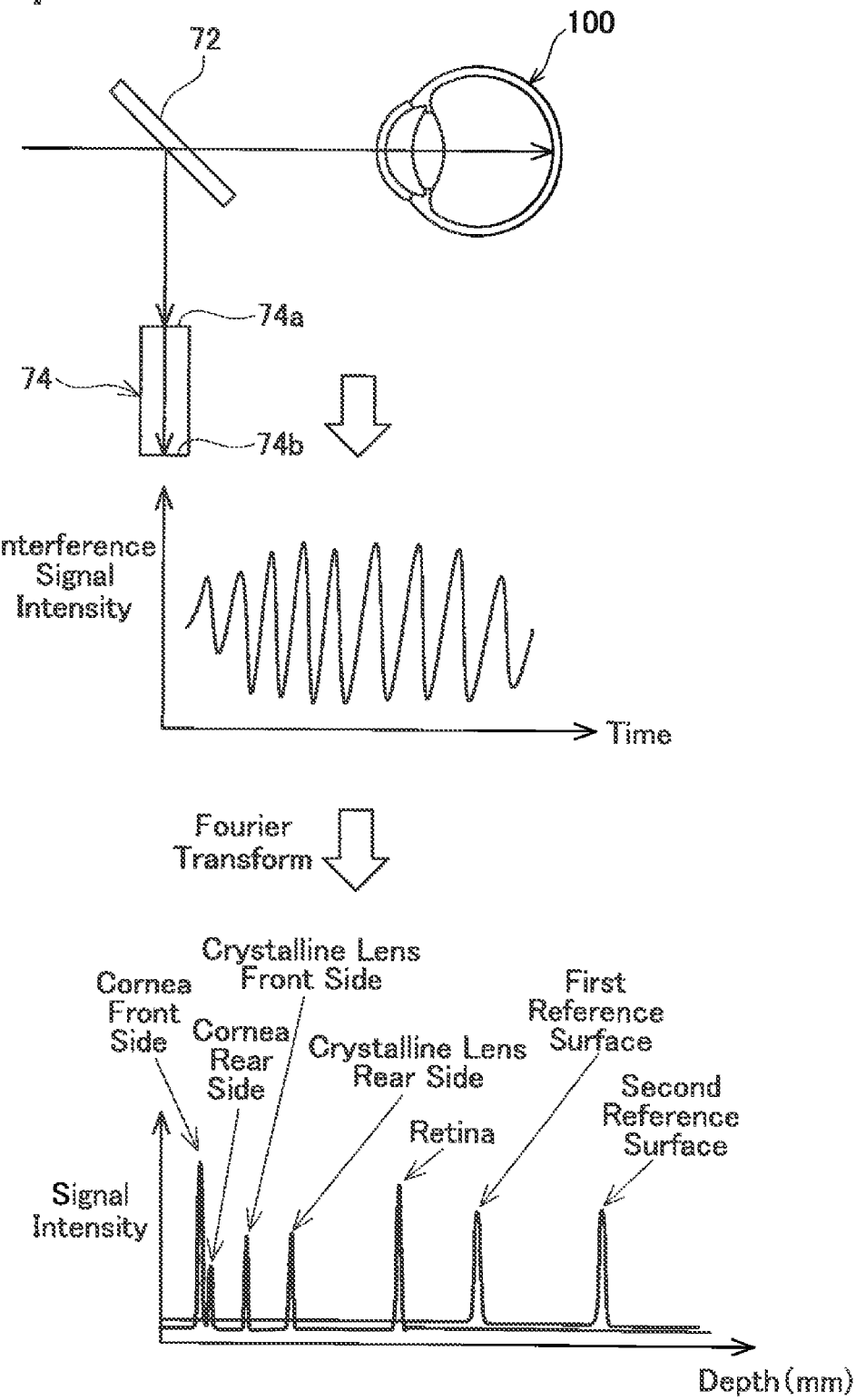
FIG. 4 is a diagram for illustrating a procedure of processing an interference signal waveform obtained when scanning an optical path length of an optical measurement system within a predetermined range of the optical path length.

Therefore, the processor 64 performs Fourier transform of the signal input from the light receiving element 26 to thereby divide, from the signal, an interference signal component depending on the reflected light reflected from each portion of the eye 100 (i.e., the front surface and rear surface of the cornea 102, the front surface and rear surface of the crystalline lens 104, the surface of the retina 106) and first and second reflection surfaces 74a and 74b (see a bottom graph in FIG. 4). Herewith, the processor 64 can specify the positions of each portion of the eye 100 and the first and second reflection surfaces 74a and 74b.

Next, the processor 64 specifies the positions of each portion (i.e., the front surface and rear surface of the cornea 102, the front surface and rear surface of the crystalline lens 104, the surface of the retina 106) of the eye 100, and the first and second reflection surfaces 74a and 74b by Fourier transforming the interference signal obtained in step S12 (S14). Herein, in the embodiment, by adjusting the position at which the optical member 74 is disposed with respect to the 0 point, peaks indicating the positions of the respective portions of the eye 100 are prevented from overlapping with peaks indicating the respective positions of the first and second reflection surfaces 74a and 74b as shown at the bottom of FIG. 4. Accordingly, the positions of respective portions of the eye 100 and the positions of the respective first and second reflection surfaces 74a and 74b can be easily specified from a signal component that is Fourier transformed.

Next, the processor 64 calculates the ocular axial length (i.e., a length from the surface of the cornea to the retina) of the eye 100 from the positions of respective portions of the eye 100 and the positions of the respective first and second reflection surfaces 74a and 74b obtained in step S14 (S16). Specifically, the processor 64 calculates the ocular axial length from the interference light by subtracting the position of the surface of the cornea from the position of the retina of the eye 100 obtained in step S14. Then, the processor 64 calculates the length from the first reflection surface 74a to the second reflection surface 74b from the interference light by subtracting the position of the first reflection surface 74a from the position of the second reflection surface 74b obtained in step S14. Herein, the length from the first reflection surface 74a to the second reflection surface 74b corresponds to the length of the optical member 74, and the length of the optical member 74 is given. Accordingly, the ocular axial length calculated from the reflection light is corrected by using the length of the optical member 74 (actual value) and the length of the optical member 74 obtained from the interference light (measurement value). Specifically, the ocular axial length is calculated by a next formula: ocular axial length (after correction)=ocular axial length obtained from interference light×(length of the optical member 74 (actual value)/length of the optical member 74 obtained from the interference light (measurement value)).

Upon calculating the ocular axial length in step S16, the processor 64 displays the calculated ocular axial length on the monitor 62 (S18). Herewith, the processing by the processor 64 is ended.

As is apparent from the above description, the ocular axial length of the eye 100 is calculated by using the interference light for measurement obtained by the optical measurement system and the interference light for calibration obtained by the optical calibration system in the ophthalmic apparatus according to the embodiment. Accordingly, even when the light output from the light source 12 is changed with time due to heat, aging change, etc., of the light source 12, the influence can be suppressed, and the ocular axial length of the eye 100 can be accurately calculated.

Furthermore, the first reflection surface 74a and the second reflection surface 74b are provided in the optical calibration system, and the ocular axial length is corrected by using a difference of the optical path lengths of the first reflection surface 74a and the second reflection surface 74b. Accordingly, even when a positional relationship between the optical member 74 and another member (e.g., the light source 12, the interferometer 20) is changed with time, and the optical path lengths from the light source 12 to the respective reflection surfaces 74a and 74b of the optical member 74 are changed, the changes do not influence the measurement of the ocular axial length. That is, a variation of the optical path length from the light source 12 to the first reflection surface 74a and a variation of the optical path length from the light source 12 to the second reflection surface 74b are same, so that the ocular axial length to be calculated is not influenced by the variations. Consequently, the ocular axial length of the eye 100 can be adequately measured.

While specific examples of the present teachings have been described above in detail, these examples are merely illustrative and place no limitation on the scope of the patent claims. The technology described in the patent claims also encompasses various changes and modifications to the specific examples described above.

Figure 6:
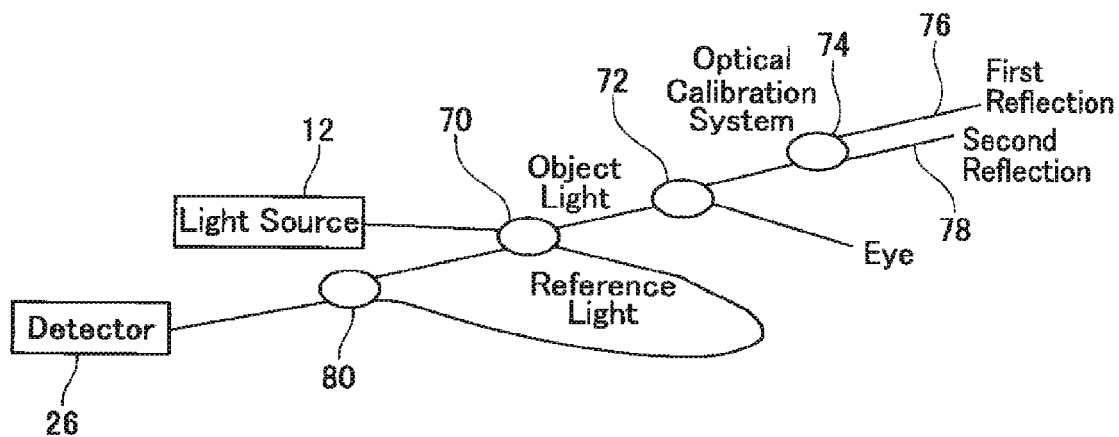
FIG. 6 is a diagram showing a configuration of an optical system of an ophthalmic apparatus according to a modification of the embodiment.

For example, in the above embodiment, the optical calibration system is configured by the optical member 74, but is not limited thereto. For example, an optical system having a configuration as shown in FIG. 6 may be employed. In the optical system shown in FIG. 6, light from the light source 12 is branched into reference light (light to be radiated on a reference surface) and object light (light to be radiated to the eye to be examined) by a coupler 70, and the branched object light is further branched into light to be radiated to the eye to be examined and light for calibration by a coupler 72. The light branched for calibration is branched into an optical fiber 76 and an optical fiber 78 by a coupler 74. The light introduced into the optical fibers 76 and 78 is reflected at end faces of the optical fibers 76 and 78, and detected by the detector (light receiving element) 26 via couplers 74, 72, 70, and 80. An optical path length of the optical fiber 76 is different from an optical path length of the optical fiber 78, so that interference light for calibration according to light reflected at the end face of the optical fiber 76 and interference light for calibration according to light reflected at the end face of the optical fiber 78 are detected by the detector 26. Therefore, an operational advantage similar to that in the above embodiment can be obtained.

Figure 7:
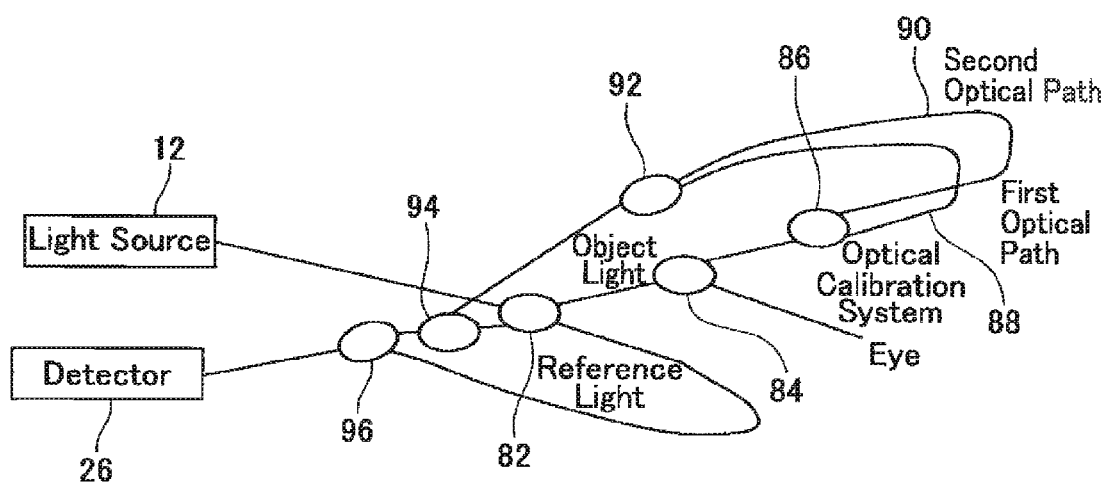
FIG. 7 is a diagram showing a configuration of an optical system of an ophthalmic apparatus according to another modification of the embodiment.

Alternatively, an optical system having a configuration as shown in FIG. 7 may be employed. In the optical system shown in FIG. 7, light from the light source 12 is branched into reference light (i.e., light to be radiated on a reference surface) and object light (light to be radiated to the eye to be examined) by a coupler 82, and the branched object light is further branched into light to be radiated to the eye to be examined and light for calibration by a coupler 84. The light branched for calibration is branched into an optical fiber 88 and an optical fiber 90 by a coupler 86. The light introduced into the optical fibers 88 and 90 is detected by the detector (light receiving element) 26 via couplers 92, 94, and 96. By differentiating optical path lengths of the optical fibers 88 and 90 and by guiding light to the coupler 94 by the optical fibers 88 and 90, interference light for calibration according to light guided by the optical fiber 88 and interference light for calibration according to light guided by the optical fiber 90 are detected by the detector 26. Therefore, an operational advantage similar to that in the above embodiment can be obtained.

In the above embodiment, the ophthalmic apparatus is of a Fourier domain method using a light source of a wavelength sweep type (so called an SS-OCT system), the ophthalmic apparatus may be of a Fourier domain method that Fourier analyzes a wave spatially generated by a white light source and a spectroscope (so called an SD-OCT system). In the above embodiment, the optical calibration system is provided on an optical axis of light radiated to the eye to be examined, the optical calibration system may be provided on an optical axis of light radiated on the reference surface. Alternatively, when two optical path sections are formed in the optical calibration system to use optical path lengths of both thereof, the optical calibration system may be disposed at any position in the optical measurement system. For example, the optical calibration system may be disposed between the hot mirror 48 and the eye 100 in FIG. 1.

Furthermore, in the above embodiment, the optical calibration system uses reflected light from two reflection surfaces 74a and 74b, but an optical calibration system using reflected light from one reflection surface may be employed. For example, two reflected light is generated by moving one reflection surface by a predetermined distance, and the two reflected light is used to correct positions of respective portions of the eye to be examined obtained from interference light for measurement.

The technical elements explained in the present description or drawings provide technical utility either independently or through various combinations. The present invention is not limited to the combinations described at the time the claims are filed. Further, the purpose of the examples illustrated by the present description or drawings is to satisfy multiple objectives simultaneously, and satisfying any one of those objectives gives technical utility to the present invention.

What is claimed is:

1. An ophthalmic apparatus comprising:
   a light source;
   a light receiving element;
   an optical measurement system configured to radiate light from the light source to an interior of an eye to be examined and guide reflected light from the eye to the light receiving element;
   an optical reference system configured to guide the light from the light source via a reference surface as reference light to the light receiving element;
   an optical calibration system configured to guide the light from the light source via one or more reflecting surfaces along one or more predetermined optical path lengths as calibration light to the light receiving element;
   the light receiving element configured to receive interference light for measurement produced by both the reflected light guided by the optical measurement system and the reference light guided by the optical reference system, and also receive interference light for calibration produced by both the calibration light guided by the optical calibration system and the reference light guided by the optical reference system; and
   a processor configured to determine a position of a measuring portion inside the eye by Fourier-analyzing the interference light for measurement, and to correct the position of the measuring portion inside the eye determined from the interference light for measurement by using a result measured from the interference light for calibration received by the light receiving element, wherein
   the optical calibration system comprises an optical member having first and second reflecting surfaces, the first reflecting surface being a first end of the optical member, and the second reflecting surface being a second end of the optical member,
   the optical calibration system includes a first optical path section a second optical path section,
   the first optical path section has a predetermined first optical path length between the light source, the first reflecting surface, and the light receiving element,
   the second optical path section has a predetermined second optical path length between the light source, the second reflecting surface, and the light receiving element,
   a difference between the first optical path length and the second optical path length is determined by a length from the first reflecting surface to the second reflecting surface,
   the light receiving element receives first interference light for calibration produced by light guided by the first optical path section and reflected light guided by the optical reference system, and second interference light for calibration produced by light guided by the second optical path section and reflected light guided by the optical reference system, and
   the processor corrects the position of the measuring portion inside the eye determined from the interference light for measurement by using a result measured from the first interference light for calibration and a result measured from the second interference light for calibration.

2. The ophthalmic apparatus according to claim 1, wherein
   the optical calibration system is designed such that an optical path length of the one or more predetermined optical path lengths is from a 0 point where an optical path length of the optical reference system and an optical path length of an optical object system are identical to each other.

3. The ophthalmic apparatus according to claim 1, wherein
   the processor further calculates an ocular axial length of the eye from a position of a cornea and a position of a retina of the eye determined from the interference light for measurement and the interference light for calibration.

4. The ophthalmic apparatus according to claim 1, wherein
   the processor further calculates an ocular axial length of the eye from a position of a cornea and a position of a retina of the eye determined from the interference light for measurement and the first interference light for calibration and the second interference light for calibration.

5. The ophthalmic apparatus according to claim 1, wherein
   the optical calibration system is configured to guide the light from the light source, along the first optical path section as first calibration light to the light receiving element,
   the optical calibration system is configured to guide the light from the light source along the second optical path section as second calibration light to the light receiving element, and
   the processor is configured to determine an optical path length difference between the first optical path section and the second optical path section and configured to correct the position of the measuring portion inside the eye based on the optical path length difference.

* * * * *